(12) United States Patent
Kessler et al.

(10) Patent No.: US 9,943,330 B2
(45) Date of Patent: Apr. 17, 2018

(54) TISSUE-REMOVING CATHETER WITH ASYMMETRIC WINDOW

(71) Applicant: Covidien LP, Mansfield, MA (US)

(72) Inventors: Jason Kessler, Minneapolis, MN (US); Lucas Schneider, Champlin, MN (US)

(73) Assignee: Covidien LP, Mansfield, MA (US)

( * ) Notice: Subject to any disclaimer, the term of this patent is extended or adjusted under 35 U.S.C. 154(b) by 190 days.

(21) Appl. No.: 14/850,302

(22) Filed: Sep. 10, 2015

(65) Prior Publication Data
US 2017/0071623 A1    Mar. 16, 2017

(51) Int. Cl.
| | | |
|---|---|---|
| *A61M 29/00* | (2006.01) | |
| *A61B 17/22* | (2006.01) | |
| *A61B 17/32* | (2006.01) | |
| *A61M 1/00* | (2006.01) | |
| *A61B 17/3207* | (2006.01) | |
| *A61B 90/00* | (2016.01) | |

(52) U.S. Cl.
CPC ........ *A61B 17/320783* (2013.01); *A61B 17/320758* (2013.01); *A61B 90/361* (2016.02); *A61B 2017/22039* (2013.01); *A61B 2017/320791* (2013.01)

(58) Field of Classification Search
CPC ........ A61B 17/3205; A61B 17/320783; A61B 17/320758; A61B 2017/00778; A61B 2017/22039; A61B 2017/320791; A61M 25/0194; A61M 25/04
USPC ........................................... 606/108
See application file for complete search history.

(56) References Cited

U.S. PATENT DOCUMENTS

| | | | |
|---|---|---|---|
| 5,423,838 A | 6/1995 | Willard | |
| 7,887,556 B2 | 2/2011 | Simpson et al. | |
| 8,359,086 B2 | 1/2013 | Maschke | |
| 2003/0125758 A1* | 7/2003 | Simpson | ........ A61B 17/320758 606/159 |
| 2007/0276419 A1* | 11/2007 | Rosenthal | ........ A61B 17/32002 606/159 |
| 2013/0296901 A1 | 11/2013 | Olson | |

FOREIGN PATENT DOCUMENTS

| | | |
|---|---|---|
| WO | WO2009005779 | 7/1997 |
| WO | WO2013172970 | 11/2013 |
| WO | WO2014039099 | 3/2014 |

\* cited by examiner

*Primary Examiner* — Katrina Stransky
*Assistant Examiner* — Marie C Black

(57) ABSTRACT

A tissue-removing catheter for removing tissue from a body lumen includes an elongate catheter body configured for insertion into the body lumen and a tissue-removing element. A side opening in the distal portion of the catheter body is defined by opposite first and second side edges, a proximal edge extending between the first and second side edges, and a distal edge opposite the proximal edge and extending between the first and second side edges. The side opening window has a longitudinal axis extending between the distal and proximal edges. The tissue-removing element is configured to move between a tissue-removing position, in which the tissue-removing element is exposed through the side opening window, and a neutral position, in which the tissue-removing element is positioned inside the distal portion of the catheter. The distal edge is asymmetric about the longitudinal axis of the side opening window.

20 Claims, 18 Drawing Sheets

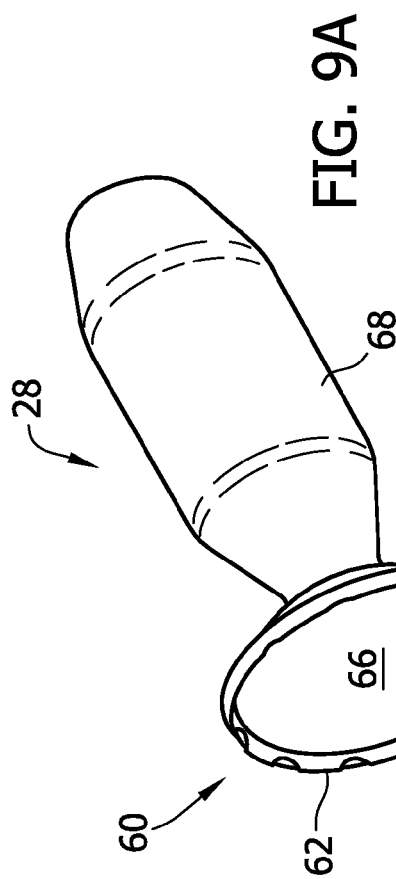
FIG. 9A
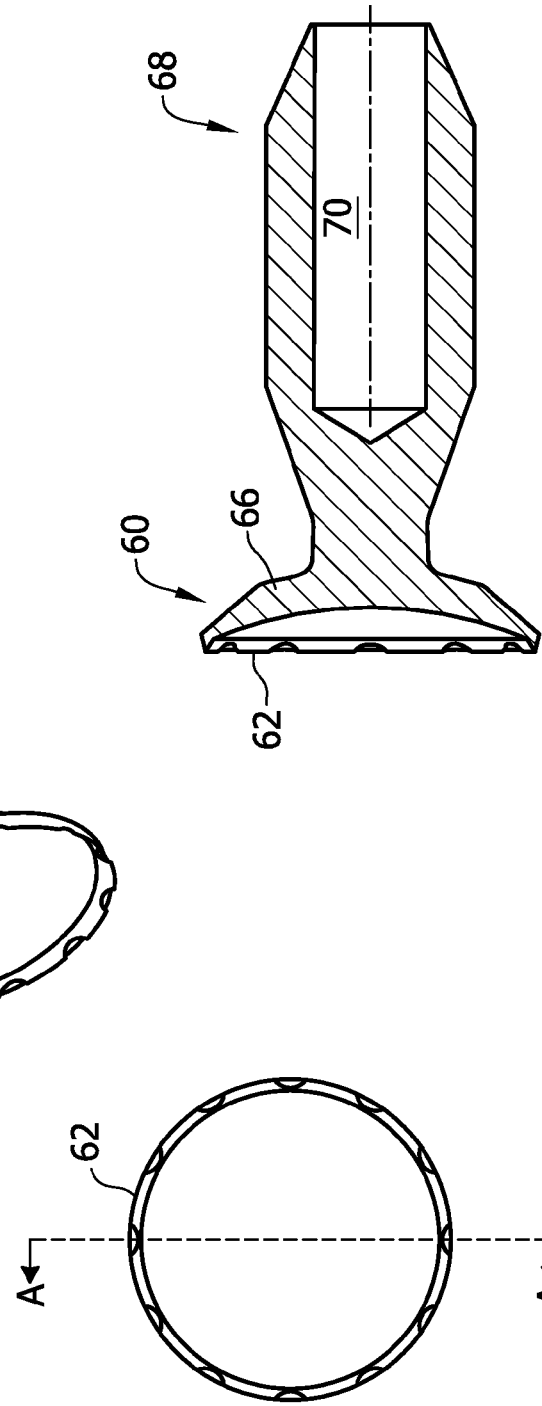
FIG. 9C
FIG. 9B

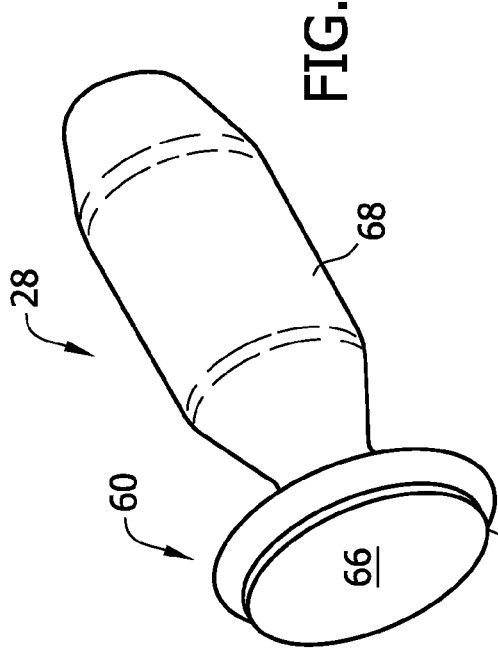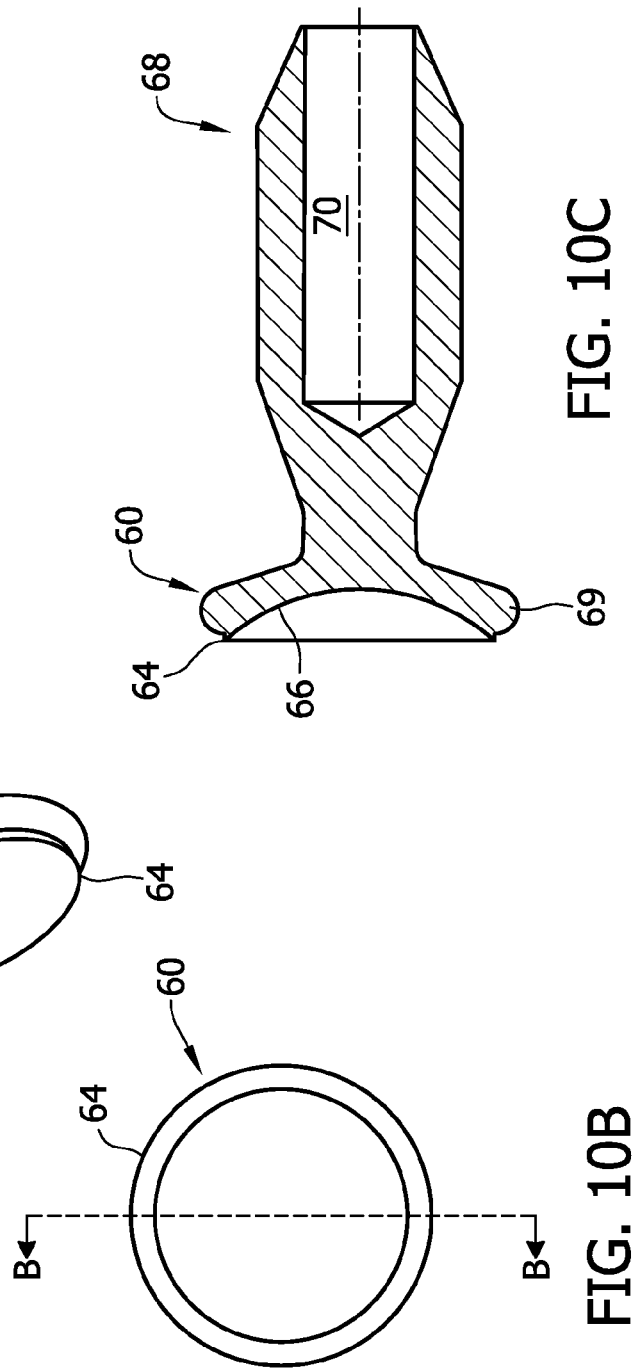

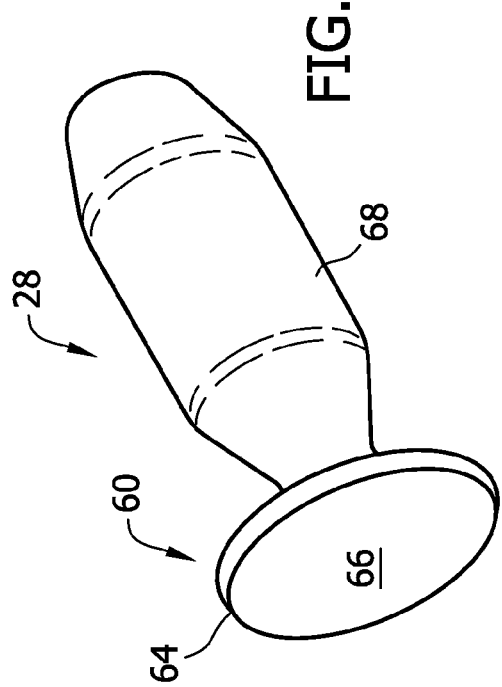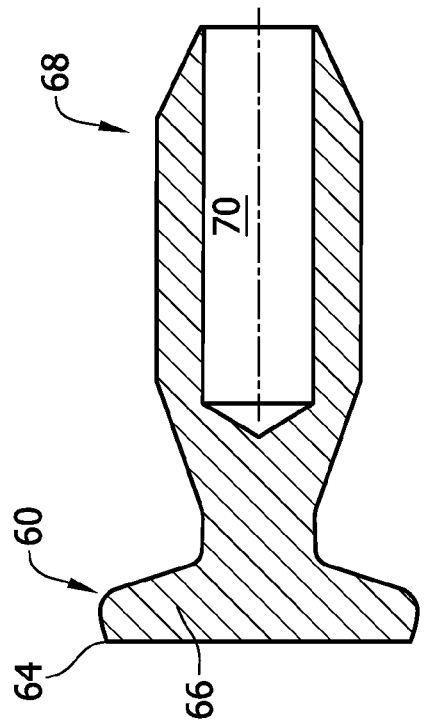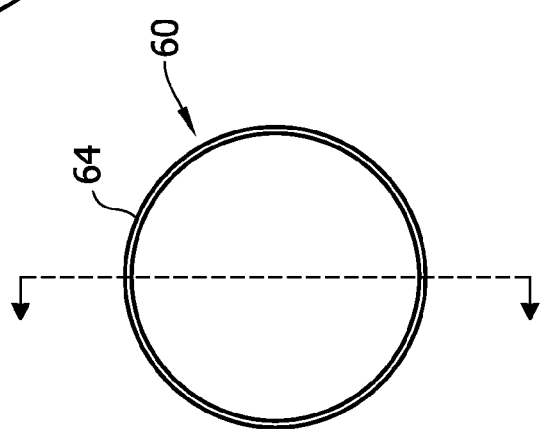
FIG. 11A
FIG. 11B
FIG. 11C

TISSUE-REMOVING CATHETER WITH ASYMMETRIC WINDOW

FIELD OF THE DISCLOSURE

Aspects of the present invention generally relate to a tissue-removing catheter for removing tissue from a body lumen.

BACKGROUND

Vascular disease frequently arises from the accumulation of atheromatous material on the inner walls of vascular lumens, particularly arterial lumens of the peripheral and other vasculature, especially peripheral arteries, resulting in a condition known as atherosclerosis. Atherosclerosis occurs naturally as a result of aging, but may also be aggravated by factors such as diet, hypertension, heredity, vascular injury, and the like. Atheromatous deposits can have widely varying properties, with some deposits being relatively soft and others being fibrous and/or calcified. In the latter case, the deposits are frequently referred to as plaque.

Vascular disease can be treated in a variety of ways, including drugs, bypass surgery, and a variety of catheter-based approaches, including those which rely on intravascular debulking or removal of the atheromatous or other material occluding a blood vessel. A variety of methods for cutting or dislodging material and removing such material from the blood vessel have been proposed, generally being referred to as atherectomy procedures. Atherectomy catheters intended to cut or excise material from the blood vessel lumen may employ a rotatable cutting blade (or other tissue-removing element) which can be advanced into or past the occlusive material in order to cut and separate such material from the blood vessel lumen.

Although atherectomy catheters have proven very successful in treating atherosclerosis, problems may arise when the tissue-removing element becomes biased or off-axis during use. If the tissue-removing element becomes biased, it can contact the catheter and cause damage to the catheter, resulting in a non-functional device.

SUMMARY

In one aspect, a tissue-removing catheter for removing tissue from a body lumen includes an elongate catheter body configured for insertion into the body lumen. The catheter body has opposite distal and proximal portions and a longitudinal axis extending between the distal and proximal portions. A side opening in the distal portion of the catheter body is defined by opposite first and second side edges, a proximal edge extending between the first and second side edges, and a distal edge opposite the proximal edge and extending between the first and second side edges. The side opening window has a longitudinal axis extending between the distal and proximal edges. A tissue removing element is located generally at the distal portion of the catheter body for rotation generally about the longitudinal axis of the catheter body. The tissue-removing element is configured to move between a tissue-removing position, in which the tissue-removing element is exposed through the side opening window, and a neutral position, in which the tissue-removing element is positioned inside the distal portion of the catheter. The distal edge is asymmetric about the longitudinal axis of the side opening window.

Other features will be in part apparent and in part pointed out hereinafter.

BRIEF DESCRIPTION OF THE DRAWINGS

FIG. 9A is a perspective view of a cutter of the present invention;

FIG. 9B is an end view of the cutter of FIG. 9A;

FIG. 9C is a sectional view of the cutter along line A-A of the cutter of FIGS. 9A and 9B;

FIG. 10A is a perspective view of a cutter of the present invention;

FIG. 10B is an end view of the cutter of FIG. 10A;

FIG. 10C is a sectional view of the cutter along line B-B of the cutter of FIGS. 10A and 10B;

FIG. 11A is a perspective view of another cutter of the present invention;

FIG. 11B is an end view of the cutter of FIG. 11A;

FIG. 11C is a sectional view of the cutter along line C-C of the cutter of FIGS. 11A and 11B;

Corresponding reference characters indicate corresponding parts throughout the drawings.

DETAILED DESCRIPTION OF THE DRAWINGS

Figure 1:
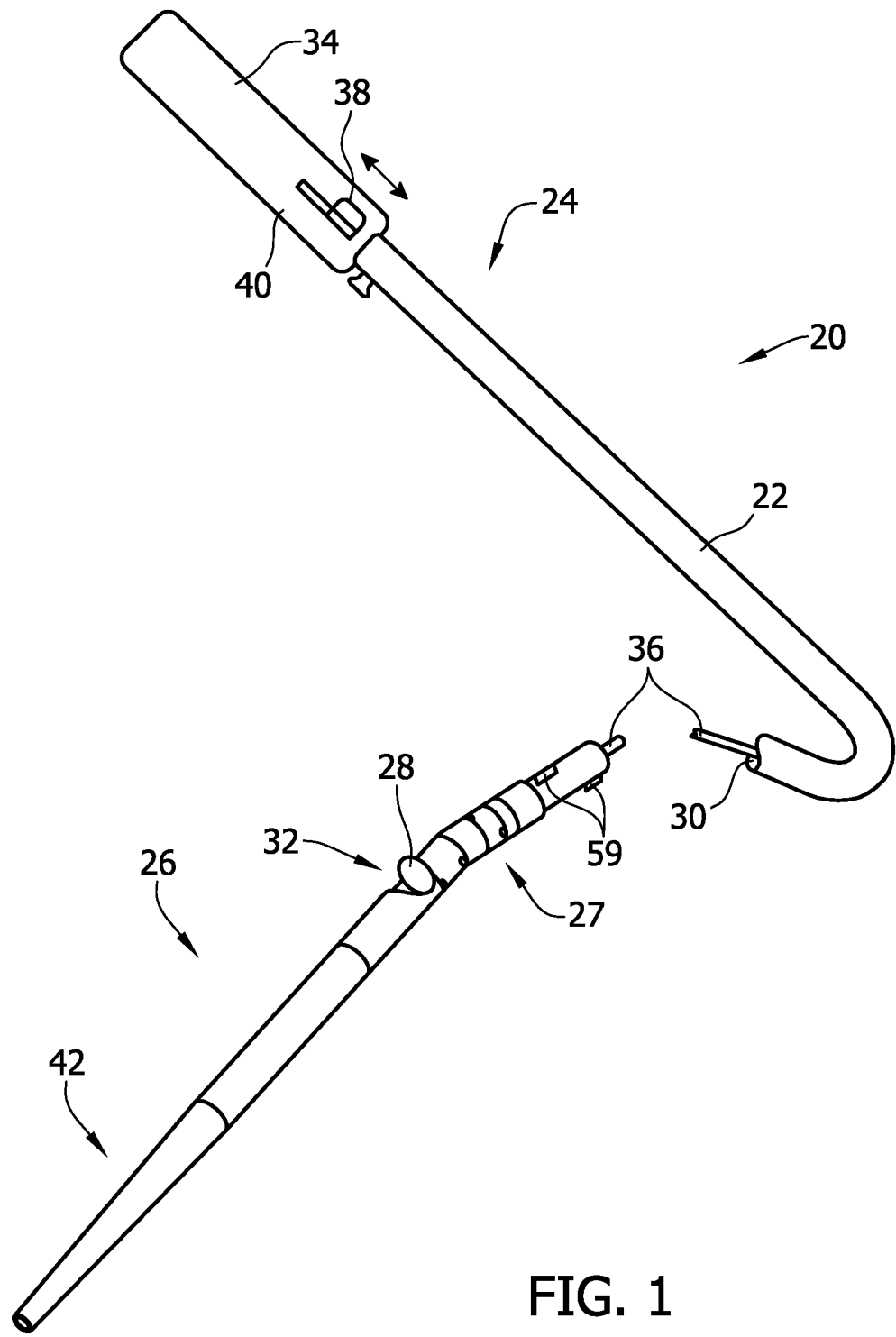
FIG. 1 is a perspective view of one embodiment of a tissue-removing catheter.

Referring now to the drawings, a tissue-removing catheter having an asymmetric window is disclosed. Referring now to FIGS. 1-19, one non-limiting example of an atherectomy catheter having an asymmetric window as disclosed below, is generally indicated at 20. It is understood that the asymmetric window disclosed below may be used with other types of catheters for removing tissue from a body lumen.

The illustrated catheter 20 comprises a catheter body 22 having a proximal portion 24 and a distal portion 26. Proximal portion 24 can be coupled to distal portion 26 with a connection assembly 27 to allow pivoting or deflection of distal portion 26 relative to proximal portion 24. A tissue-removing element 28, such as a cutter, as illustrated, is disposed within a lumen 30 of the distal portion 26, whereby the distal portion functions as a tissue-removing housing. The tissue-removing element 28 removes tissue from the lesion or obstruction. It is understood that the tissue-removing element 28 may be another type of element for removing tissue, other than the illustrated cutter, including for example, an abrasive element (e.g., a burr). The cutter 28 is typically rotatable about an axis that is parallel to the longitudinal axis of the proximal portion 24 of catheter 20 and axially movable along the longitudinal axis of the distal portion 26. The cutter 28 can access target tissue through a side opening window 32 in the distal portion 26, which is typically large enough to allow the cutter 28 to protrude through and move out of the window 32 a predetermined distance. The cutter is coupled to a handle, generally indicated at 34 (FIGS. 12-16), through a coiled drive shaft 36. Actuation of an input device or manual actuator 38 on the handle, which forms part of the deployment mechanism in this embodiment, can activate the drive shaft 36 and cutter 28, and move the cutter 28 longitudinally over a cam so as to deflect the distal portion and move the cutter 28 out of cutting window 32. As explained in more detail below, camming of the cutter 28 can cause the distal portion 26 to pivot or deflect relative to the proximal portion 24 so as to deflect and urge the cutter into the tissue in the body lumen.

In some embodiments, the distal portion 26 of the catheter may be moved to an angled or offset configuration from the longitudinal axis of the proximal portion 24 of the catheter and the cutter 28. In some embodiments, the cutter 28 can also be deflected off of the axis of the proximal and/or distal portion of the catheter. Moving the distal portion 26 to an angled/offset position may cause a portion of the catheter 20 to urge against a target tissue, may expose the cutter 28 through the window 32 or both, in various embodiments.

The proximal portion 24 of the catheter body 22 may be relatively flexible and at least a portion of the distal portion 26 may be relatively rigid. Additionally, many embodiments include a flexible distal tip member 42. The flexible proximal portion 24 of the catheter is typically a torque shaft and at least a portion of the distal portion 26 is typically a rigid tubing. The torque shaft, which is indicated by the same reference numeral 24, facilitates transportation of the catheter body 22 and cutter 28 to the diseased site. The proximal end of the torque shaft 24 is coupled to the handle 34 and the distal end of the torque shaft is attached to the distal, rigid portion 26 of the catheter 20 through the connection assembly 27. The drive shaft 36 is movably positioned within the torque shaft 24 so as to rotate and axially move within the torque shaft 24. The drive shaft 36 and torque shaft 24 are sized to allow relative movement of each shaft without interfering with the movement of the other shaft. The catheter body 22 will have the pushability and torqueability such that torqueing and pushing of the proximal end will translate motion to the distal portion 26 of the catheter body 22.

Figure 1A:
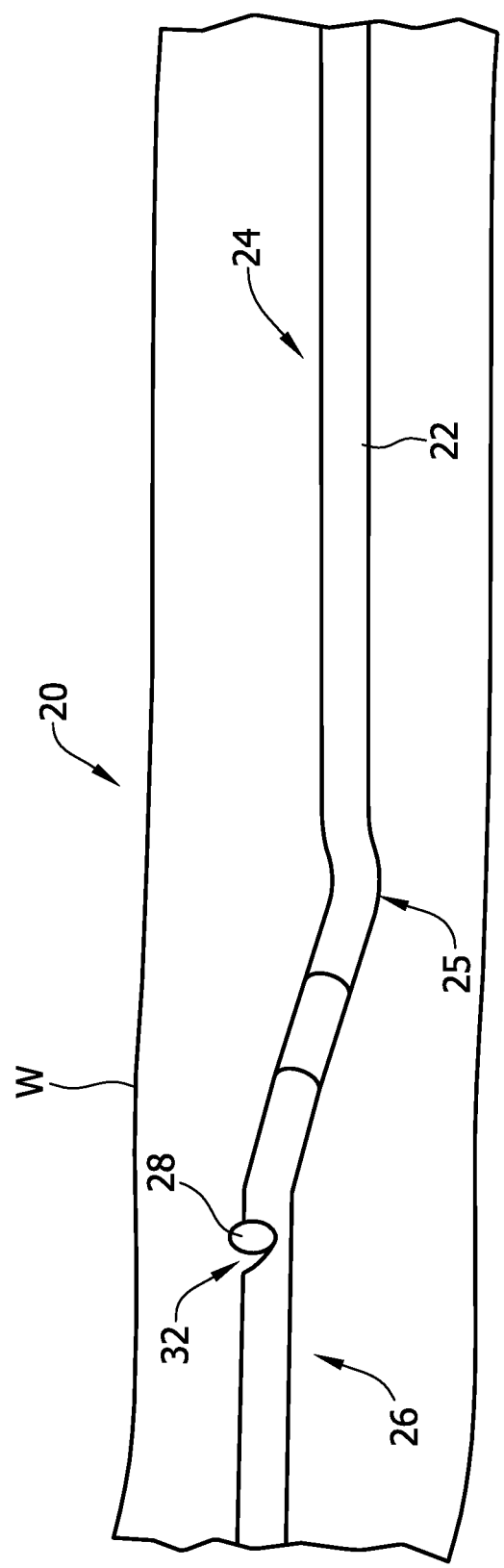
FIG. 1A is a side view of a portion of a tissue-removing catheter as in FIG. 1 in a body lumen, where the body has a distal portion with a bend, according to one embodiment of the present invention.

Referring now to FIG. 1A, the catheter 20 as in FIG. 1 may have a flexible proximal portion 24 which additionally includes urging means 25. As shown in FIG. 1A, urging means 25 may comprise a bent or curved shape towards the distal end of proximal portion 24, which may help urge the cutter 28 or other tissue-removing element toward a wall of a body lumen to enhance treatment. Such a bend increases the working range of the catheter by allowing the cutter to be urged into a lumen wall across a wider diameter.

In other embodiments, urging means 25 may take many other suitable forms. For example, a similar result to the bend may be achieved by including a distal portion that is not permanently bent but that is more rigid on one side than on the opposite side of catheter body 22. Thus, when proximal tension is applied to the proximal portion 24, as when proximal force is applied to the tissue-removing apparatus to expose the cutter 28 through the window 32, the urging means 25 will cause the catheter body 22 to bend toward the less rigid side. The less rigid side will typically be the same side as the window 32, so that the window 32 and/or the cutter 28 will be urged against a wall of a body lumen by the bend. In still other embodiments, a shaped element may be introduced into catheter body 22 to act as urging means 25. Any suitable urging means is contemplated.

Figure 2:
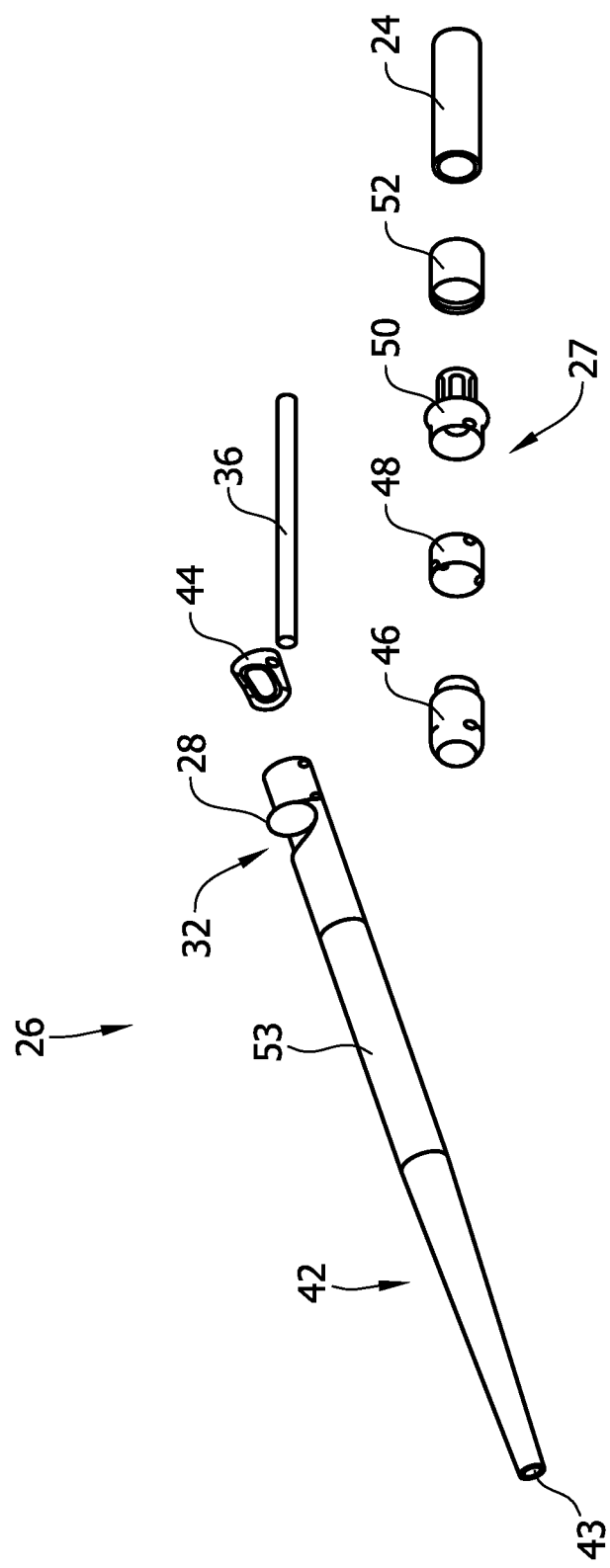
FIG. 2 is an exploded view of an exemplary distal portion of the tissue-removing catheter.

Referring to FIG. 2, the distal portion 26 includes a distal tip member 42 forming the distal end of the catheter 20 and a collection chamber 53 for storing the severed atheromatous material. The distal tip member 42 defines a lumen that can receive the guidewire. The distal tip member 42 can have a distal opening 43 that is sized to allow an imaging guidewire or conventional guidewire (not shown) to be advanced distally through the tip member. For example, some embodiments may include a distal guidewire lumen having a length of between about 1.0 cm and about 5.0 cm, and preferably between about 2.0 cm and about 3.0 cm. Such a distal guidewire lumen may be used alone or in conjunction with a proximal guidewire lumen located on another, more proximal, portion of the catheter 20.

A ramp or cam 44 can at least partially fit within the distal portion 26 of the catheter 20. As will be described in detail below, in many embodiments proximal movement of the cutter 28 over the ramp 44, causes the deflection of the distal housing 26 and guides cutter out of cutting window 32. Attached to the ramp 44 is a housing adaptor 46 that can connect one or more articulation members 48 to the distal tip member 42 to create an axis of rotation of the distal portion 26. The housing adaptor 46 and articulation member 48 allow the distal portion 26 of the catheter 20 to pivot and bias against the body lumen. In the illustrated embodiment there are only one housing adaptor 46 and one articulation member 48, but it should be appreciated that the catheters of the present invention can include, two, three, or more joints (e.g., axis of rotation), if desired. Moreover, the axes of rotation can be parallel or non-parallel with each other.

The catheter 20 can also include a shaft adaptor 50 and collar 52 to couple articulation members 48 to the torque shaft 22. Shaft adaptor 50 can connect the housing to the torque shaft 22 and the collar 52 can be placed over a proximal end of the shaft adaptor and crimped for a secure attachment. It should be appreciated by one of ordinary skill in the art that while one catheter embodiment has the above components that other catheters may include more or fewer of the components described above. For example, some components can be made integral with other components and some components may be left out entirely. Thus, instead of having a separate ramp 44, the ramp may be integrated with the distal portion 26 to direct the cutter 28 out of the cutting window 32.

As shown in FIGS. 3-5, the cutter 28 will generally be movable between two or more positions using a deployment mechanism. In the illustrated embodiment, the actuator 38 actuates operation of the deployment mechanism, although in other embodiment, the deployment mechanism may be actuated by other actuators. In the illustrated embodiment, the deployment mechanism allows for the cutter 28 to be selectively moveable to a stowed or neutral position (FIGS. 3A and 3B) in which the cutter is stowed in the distal portion 26 of the catheter body 22 and is not exposed through the window 32. In some embodiments, an imaging device (not shown) can be coupled to cutter 28 so as to image the body lumen through cutting window 32 when cutter is in the neutral position. Once the catheter 20 has reached the target site, the cutter 28 can be moved proximally to a tissue-removing position (FIGS. 4A and 4B), in which the cutter 28 extends through the cutting window 32 a distance L1 beyond an outer diameter D of the distal portion 26. In some embodiments, in the tissue-removing position, the cutter 28 will have deflected the distal portion 26 and the cutter's axis of rotation will generally be in line with connection assembly 27 but angled or offset from longitudinal axis of the distal portion of the catheter body 22.

Figure 5A:
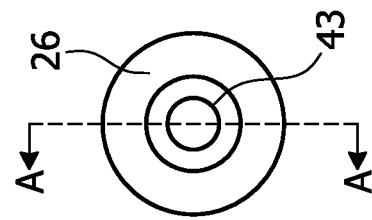
FIG. 5A is an end view of the distal portion of the tissue-removing catheter of FIG. 1 in which the cutter is in a packing position within a tip member of the catheter.
Figure 5B:
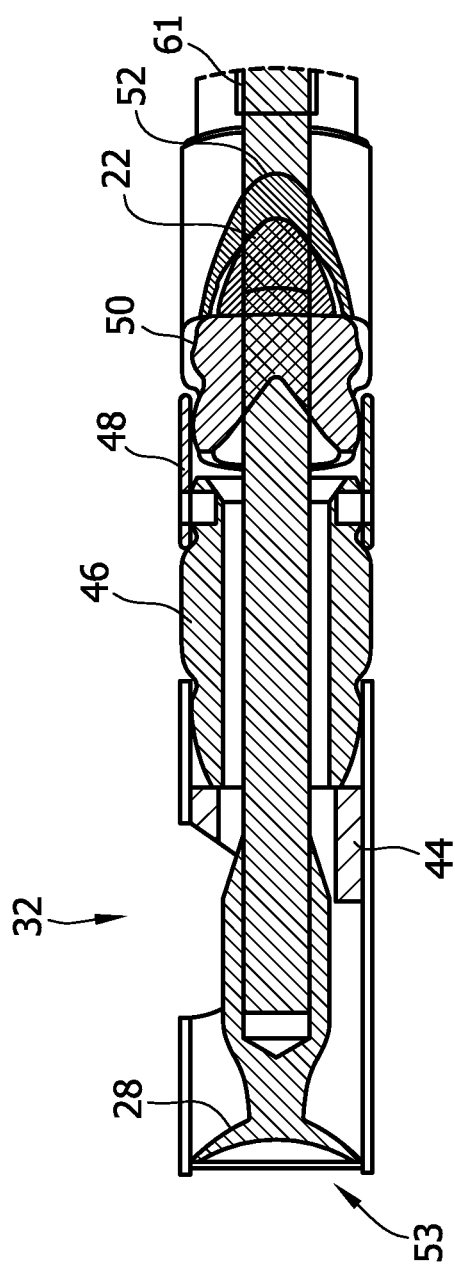
FIG. 5B is a sectional view along line A-A of FIG. 5A.

Optionally, in some embodiments, the cutter 28 can be moved to a packing position, in which the cutter is moved distally, beyond the stowed or neutral position, so as to pack the severed tissue into the distal collection chamber 53 (FIGS. 5A and 5B). It should be appreciated however, that while the exemplary embodiment moves the cutter 28 to the above described positions, in other embodiments the cutter can be positioned in other relative positions. For example, instead of having the neutral position distal of the cutting window, the neutral position may be proximal of the window, and the open position may be along the distal end of the cutting window, or the like.

Figure 3A:
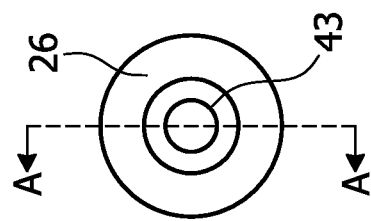
FIG. 3A is an end view of the distal portion of the tissue-removing catheter of FIG. 1 in which the cutter is in a closed position in the catheter body.
Figure 3B:
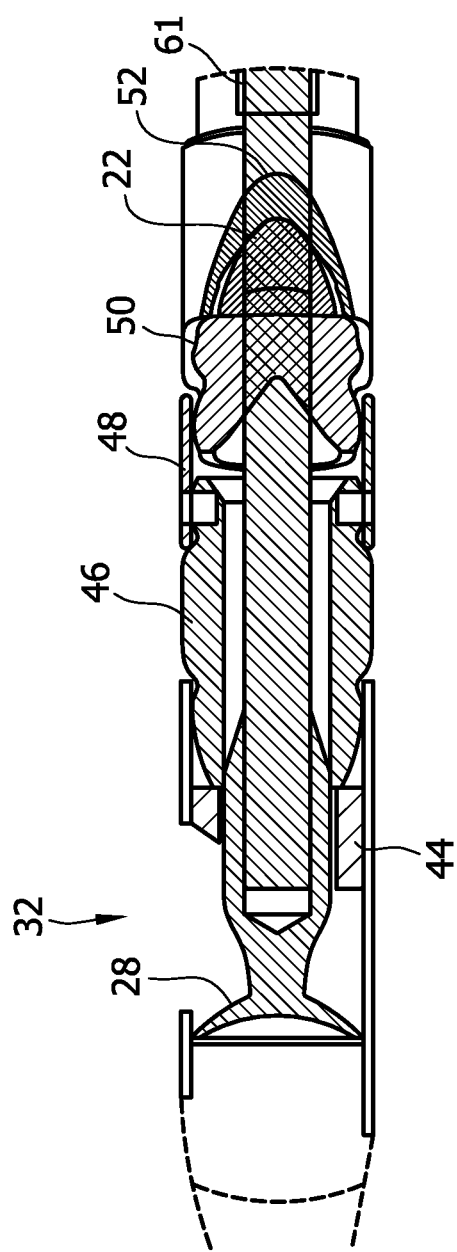
FIG. 3B is a sectional view along line A-A of FIG. 3A.
Figure 17:
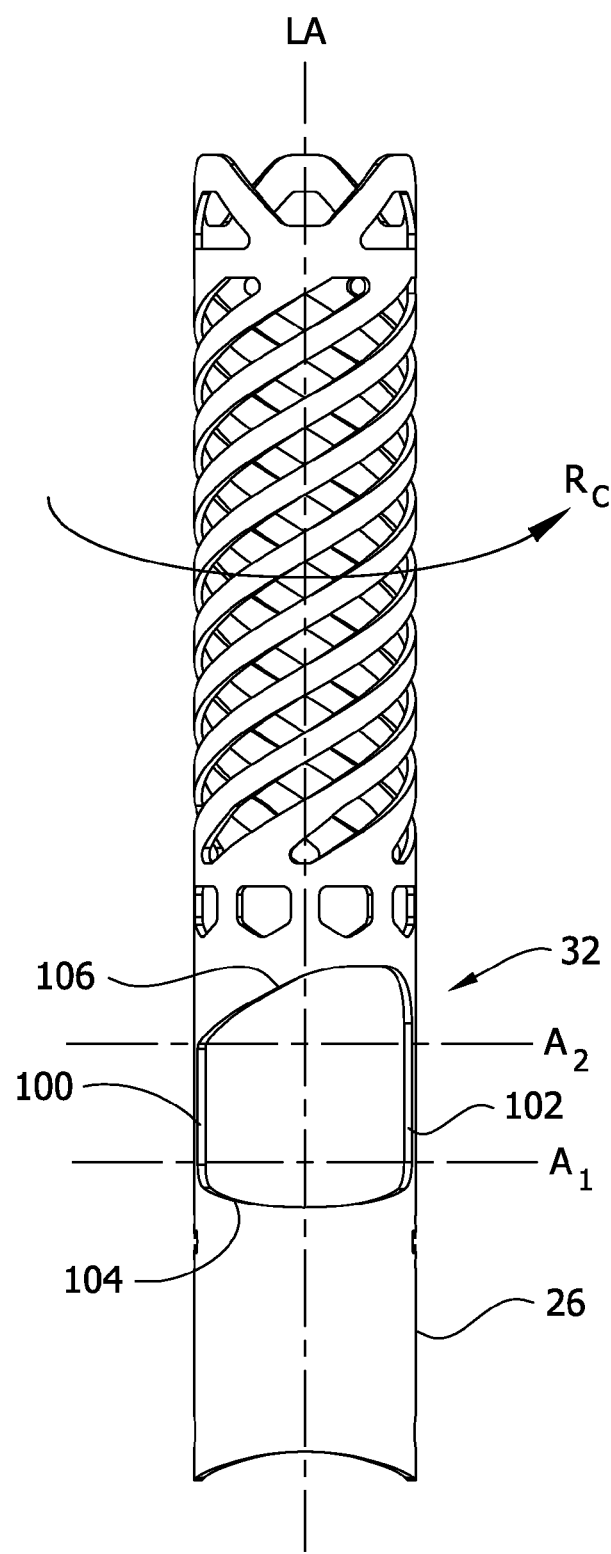
FIG. 17 is a top plan of the distal portion of the tissue-removing catheter, illustrating an asymmetric window thereof.

Referring again to FIGS. 4A and 4B, the interaction of the components of the rigid distal portions 26 in one exemplary embodiment will be further described. As shown in FIG. 4B, the cutting window 32 is typically a cutout opening in the distal portion 26. While the size of the cutting window 32 can vary, the cutting window should be long enough to collect tissue and circumferentially wide enough to allow the cutter 28 to move out of the cutting window during cutting, but sized and shaped to not expel emboli into the vasculature. As shown in FIG. 17 and described in more detail below, the cutting window 32 is asymmetric to prevent contact of the cutter 28 with a distal edge of the window during movement of the cutter from the tissue-removing position (FIGS. 4A and 4B) to the stowed or neutral position (FIGS. 3A and 3B), as described in detail below. The cams or ramp 44 (shown most clearly in FIG. 4B) can be disposed in the distal portion 26 of the catheter body 22 to guide or otherwise pivot the cutter 28 out of the cutting window 32, from the non-exposed, neutral position (FIG. 3B) to the exposed, tissue-removing position (FIG. 4B) as the cutter 28 is pulled proximally through tensioning of drive shaft 36 via the actuator 38. This operation is explained in detail below.

Figure 4A:
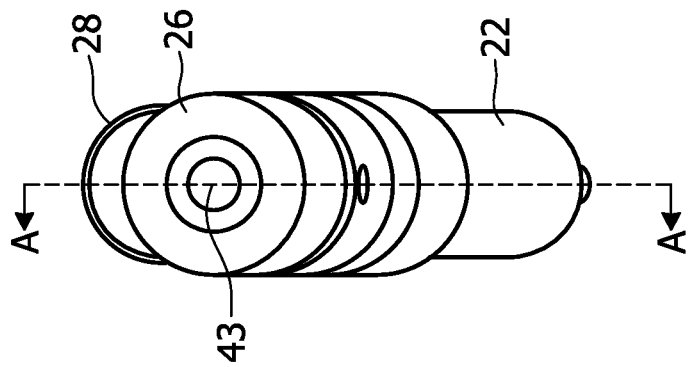
FIG. 4A is an end view of the distal portion of the tissue-removing catheter of FIG. 1 in which the cutter is in an open position outside of the cutting window.
Figure 4B:
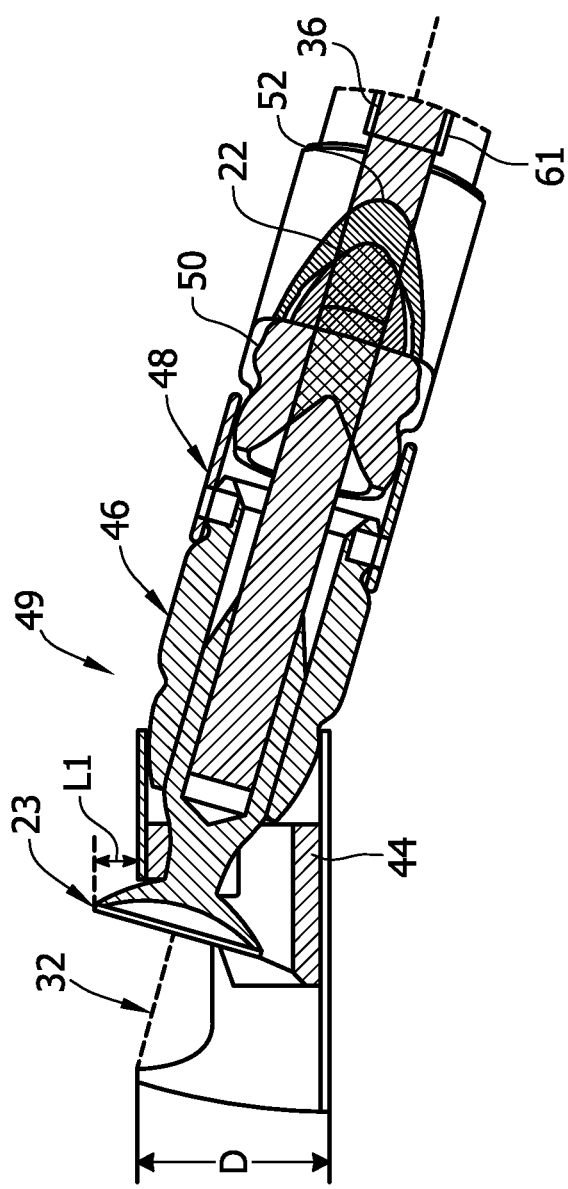
FIG. 4B is a sectional view along line A-A of FIG. 4A.

Referring to FIGS. 4A and 4B, a joint 49 is located proximal to the cutting window 32 to provide a pivot point for camming of the distal portion 26 relative to the proximal portion 24. The bending at the joint 49 is caused by the interaction of the cams or ramps 44 with cutter 28 and the tensile force provided through drive shaft 36. In the exemplary configuration, the joint 49 includes a housing adaptor 46 that is pivotally coupled to the distal rigid portion 26. As shown in FIGS. 4A and 4B, the resulting pivoting of the rigid distal portion 26 relative to the proximal portion 24 causes a camming effect which urges the distal portion against the body lumen wall without the use of urging means (e.g., a balloon) that is positioned opposite of the cutting window 32. Thus, the overall cross sectional size of the catheter body 22 can be reduced to allow the catheter 20 to access lesions in smaller body lumens. In exemplary embodiments, the distal portion 26 can deflect off of the axis of the proximal portion 24 of the catheter 20 typically between 0° degrees and 30° degrees, usually between 5° degrees and 20° degrees, and most preferably between 5° degrees and 10° degrees. The angle of deflection relates directly to the urge. Urge, however, does not necessarily relate to force but more to the overall profile of the catheter 20. For example, the greater the angle of deflection, the larger the profile and the bigger the lumen that can be treated. The ranges were chosen to allow treatment of vessels ranging from less than 2 mm to greater than 3 mm within the limits of mechanical design of the components. It should be appreciated however, that the angles of deflection will vary depending on the size of the body lumen being treated, the size of the catheter, and the like.

In some embodiments, the deflection of the distal portion 26 of the catheter 20 urges the cutter 28 into the exposed, tissue-removing position (FIG. 4B), such that distal advancement of the entire catheter body 22 can move the rotating cutter through the occlusive material. Because the cutter 28 is moved a distance L1 beyond the outer diameter of the distal portion 26 of the catheter 20 and outside of the cutting window 32, the user does not have to invaginate the tissue into the cutting window. In some embodiments, for example, the cutter 28 can be moved between about 0.025 mm and about 1.016 mm, and preferably between about 0.025 mm and about 0.64 mm, beyond the outer dimension of the distal portion 26. It should be appreciated that the cutter excursion directly relates to the depth of cut. The higher the cutter 28 moves out of the cutting window 32 the deeper the cut. The ranges are chosen around efficacy without risk of perforation of the body lumen.

Figure 3C:
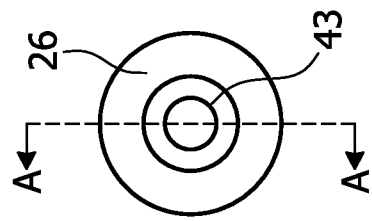
FIGS. 3C and 3D are views of the distal portion of a tissue-removing catheter, where the distal portion has a locking shuttle mechanism.
Figure 3D:
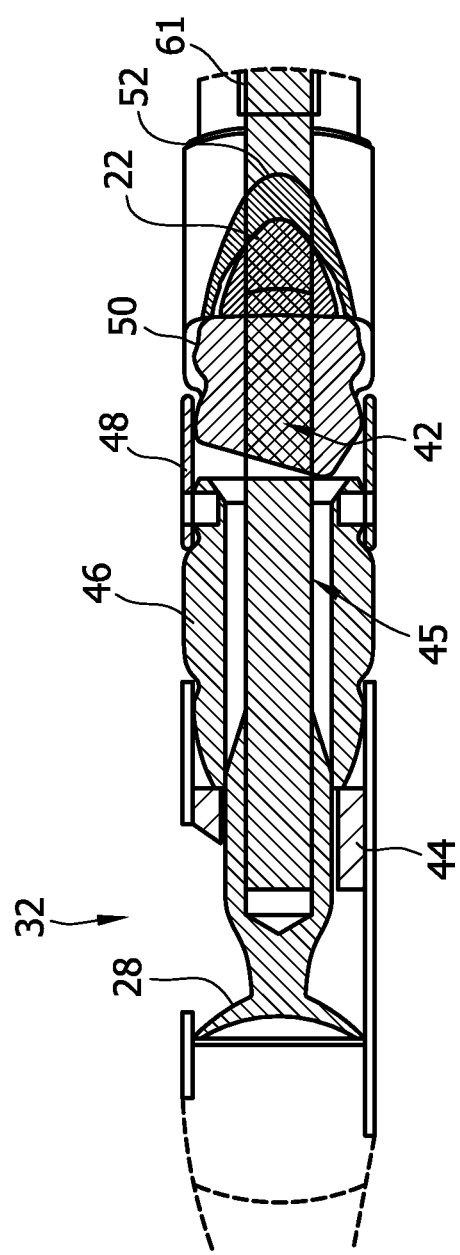
Figure 4C:
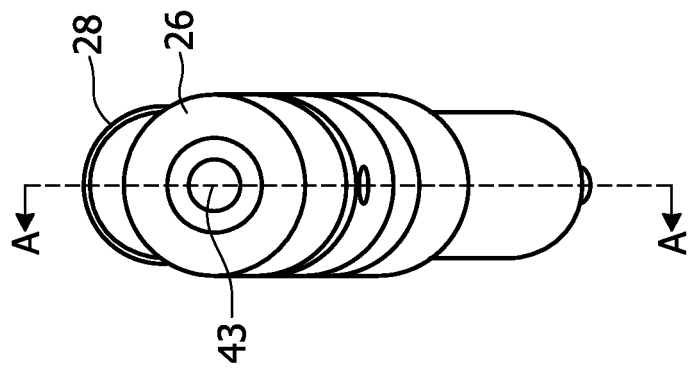
FIGS. 4C and 4D are views of the distal portion of a tissue-removing catheter in which the cutter is in an open position, where the distal portion has a locking shuttle mechanism.
Figure 4D:
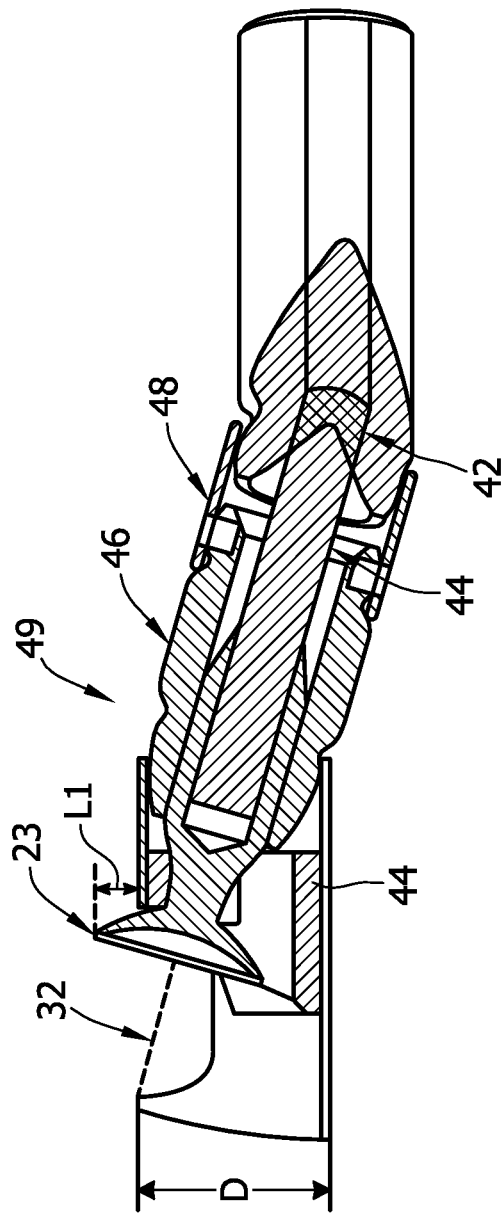

Some embodiments of the catheter 20 include a shuttle mechanism or other similar mechanism for temporarily locking the catheter in the tissue-removing position. FIGS. 3C and 3D illustrate such an embodiment in the neutral, non-tissue-removing position. Such embodiments generally include a shuttle member 45 and a shuttle stop member 42. The shuttle stop member is typically disposed at an angle, relative to a longitudinal axis through the catheter. FIGS. 4C and 4D show the same embodiment in the tissue-removing position. When the cutter 28 is moved into the tissue-removing position in such embodiments, the shuttle member 45 falls into the shuttle stop member 42 and thus locks the cutter 28 in the tissue-removing position. To unlock the cutter 28, the cutter may be advanced forward, distally, to release the shuttle member 45 from the shuttle stop member 42.

Some embodiments including a shuttle mechanism will also include two joints in the catheter body 22. Thus, catheter body 22 will include the distal portion 26, the proximal portion 24 and a middle portion. When shuttle mechanism is activated to expose cutter 28 through window 32, the middle portion may orient itself at an angle, relative to the proximal and distal portions, thus allowing cutter to be urged towards a side of a lumen. Such a two-jointed configuration may provide enhanced performance of the catheter 20 by providing enhanced contact of the cutter 28 with material to be debulked form a body lumen.

Pushing the entire catheter 20 across a lesion removes all or a portion of the lesion from the body lumen. Severed tissue from the lesion is collected by directing the removed tissue into the collection chamber 53 in the tip member 42 via the cutter 28. Once the catheter 20 and cutter 28 have moved through the lesion, the cutter can be advanced distally to "part off position" the lesion. During "parting off", the cutter 28 is moved distally from the tissue-removing position back into the cutting window 32 (FIG. 3B) and to its neutral or stowed position. The asymmetric configuration of the cutting window 32 prevents interaction of the cutter 28 with the distal edge of the cutting window during "parting off" (i.e., during movement of the cutter from the tissue-removing position to the stowed position), as described in detail below. The collection chamber 53 of the tip member 42 acts as a receptacle for the severed material, to prevent the severed occlusive material from entering the body lumen and possibly causing downstream occlusions. After "parting off", the cutter 28 can be moved distally to a packing position, in which the cutter moves distally within the collection chamber 53 to pack the severed tissue into collection chamber 53 (FIG. 3B). Typically, the collection chamber 53 will be large enough to allow multiple cuts to be collected before the catheter 20 has to be removed from the body lumen. When the collection chamber 53 is full, or at the user's discretion, the catheter 20 can be removed, emptied and reinserted over the guidewire.

In various embodiments, enhancements to the collection chamber 53 may be included. For example, in some embodiments the collection chamber 53 may be configured to be partially or completely translucent or radiolucent and a portion of the catheter 20 surrounding or adjacent to the window 32 will be radiopaque. This combination of radiolucent collection chamber 53 and radiopaque material adjacent window 32 will enhance the ability of a user to determine how full the collection chamber 53 is, because the fullness of the collection chamber will be directly related to the distance the cutter 28 can advance forward into the collection chamber 53. By facilitating the assessment of collection chamber filling, these embodiments will reduce the need for manually withdrawing the catheter to examine the collection chamber 53.

Figure 6:
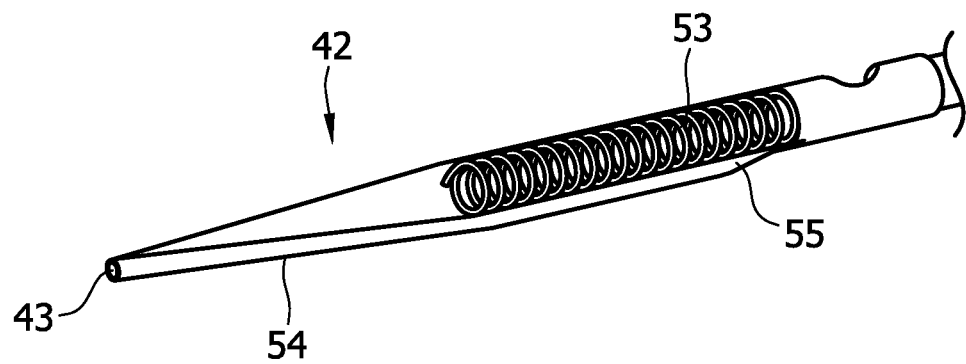
FIGS. 6 to 8 illustrate a monorail delivery system of the present invention.
Figure 7:
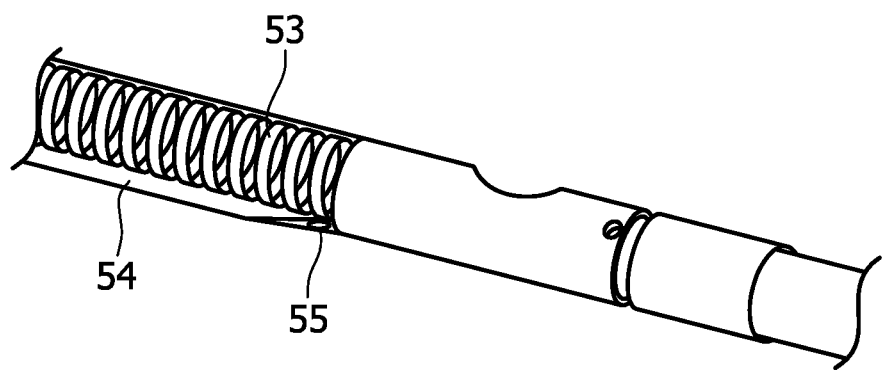
Figure 8:
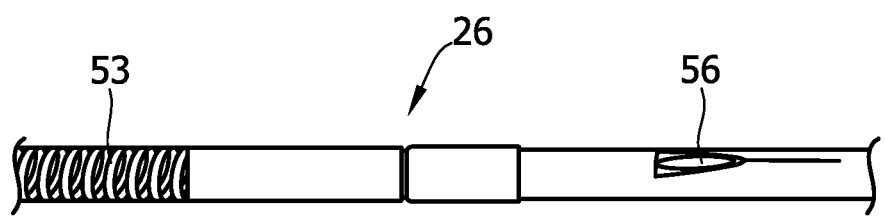

FIGS. 6 through 8 illustrate one exemplary monorail delivery system to assist in positioning the cutter 28 at the target site. For example, tip member 42 of the catheter can include a lumen 54 having a distal opening 43 and a proximal opening 55 that is sized to receive a guidewire, having a diameter of about 0.014 in. (0.3556 mm), about 0.018 in. (0.4572 mm), about 0.032 in. (0.8128 mm), or any other suitable diameter.

The catheters 20 can include radiopaque markers so as to allow the user to track the position of the catheter under fluoroscopy. For example, as already described, a point or area around or adjacent to the window 32 may be made radiopaque. In other embodiments, the distal portion 26 can be radiopaque and radiopaque markers can be disposed on the flexible shaft 36. Typically, the markers will be disposed along the top, proximal to the cutting window 32, and on the bottom of the catheter 20 to let the user know the position of the cutter and cutting window relative to the target site. If desired, the top and bottom markers can be different shaped so as to inform the user of the relative orientation of the catheter 20 in the body lumen. Because the guidewire will form a helix in its transition from lumen 56 to tip member lumen 54, the user will be able to view the top and bottom radiopaque markers without interference from the guidewire. Some embodiments of the catheter 20 can also include a radiopaque cutter stop 61 (FIG. 3B) that is crimped to driveshaft 36 proximal of the cutter that moves with the cutter so as to let the user know when the cutter 28 is in the open position.

FIGS. 9A through 11D show some exemplary embodiments of the cutter 28. The distal portion 60 of the rotatable cutter 28 can include a serrated knife edge 62 or a smooth knife edge 64 and a curved or scooped distal surface 66. The distal portion 60 may have any suitable diameter or height. In some embodiments, for example, the diameter across the distal portion 60 may be between about 0.1 cm and about 0.2 cm. A proximal portion 68 of the cutter 28 can include a channel 70 that can be coupled to the drive shaft 36 that rotates the cutter. As shown in FIGS. 10A-10C, some embodiments of the cutters 28 can include a bulge or bump 69 that is provided to interact with a stent so as to reduce the interaction of the cutting edge with the stent. In any of the foregoing embodiments, it may be advantageous to construct a serrated knife edge 62, a smooth knife edge 64, or a scooped distal surface 66 out of tungsten carbide.

Figure 11D:
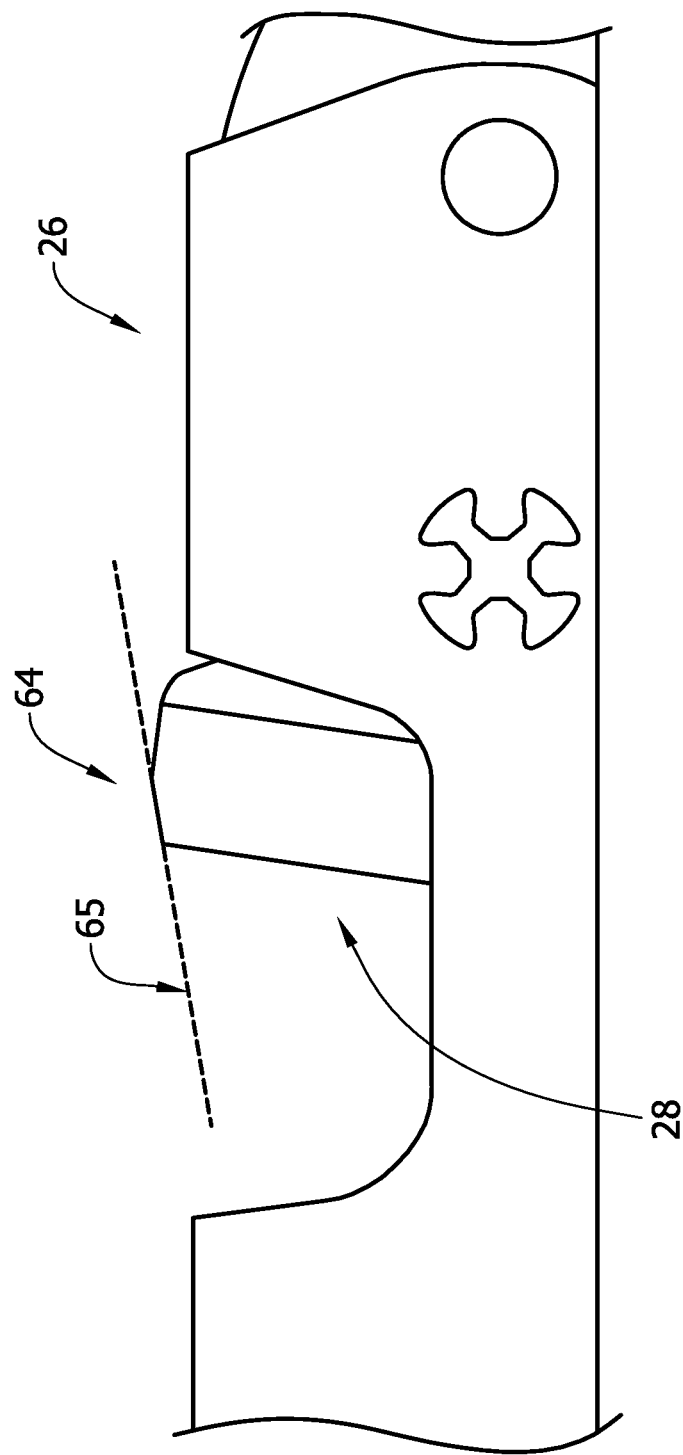
FIG. 11D is a side view of another embodiment of a cutter, shown partially within a catheter body.
Figure 12:
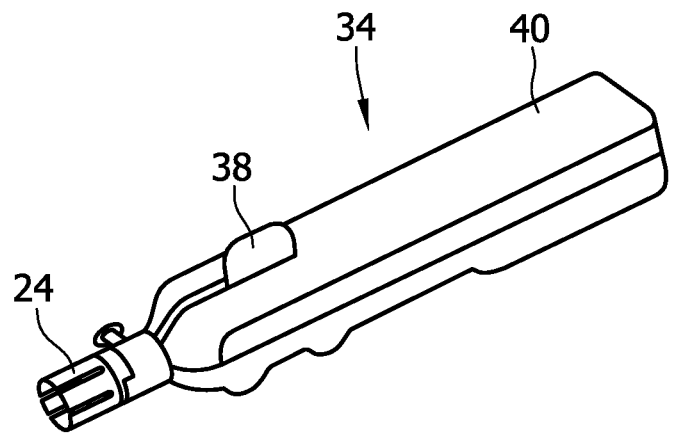
FIG. 12 is a perspective of an embodiment of a handle for the tissue-removing catheter.
Figure 13:
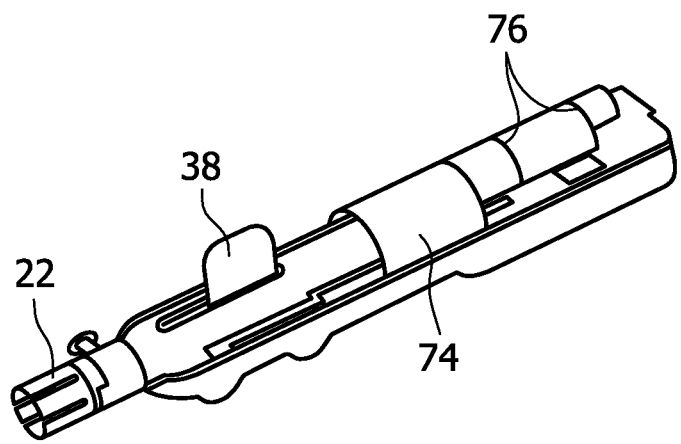
FIG. 13 is similar to FIG. 12 with a cover of the handle removed.
Figure 14:
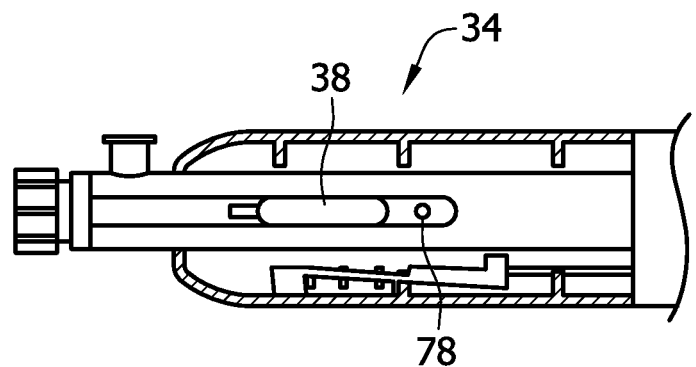
FIG. 14 illustrates a neutral position of a lever of the handle.
Figure 15:
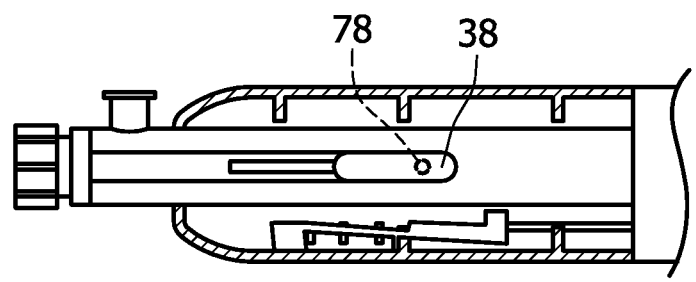
FIG. 15 illustrates a tissue-removing position of the lever of the handle.
Figure 16:
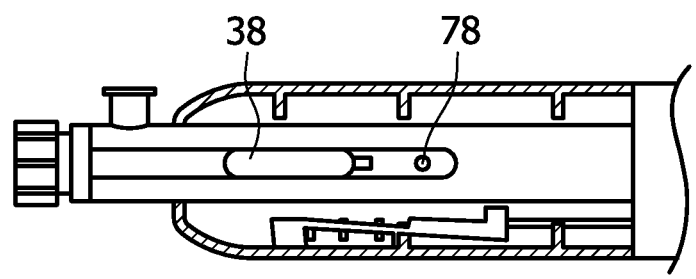
FIG. 16 illustrates a packing position of the lever of the handle.

Another embodiment of a cutter 28 shown in side view within a distal portion 26 in FIG. 11D. In this embodiment, the cutter 28 has a beveled edge 64, made of tungsten carbide, stainless steel, titanium or any other suitable material. The beveled edge 64 is angled inward, toward the axis of rotation (or center) of the cutter 28, creating a "negative angle of attack" 65 for the cutter 28. Such a negative angle of attack may be advantageous in many settings, when one or more layers of material are desired to be debulked from a body lumen without damaging underlying layers of tissue. Occlusive material to be removed from a vessel typically has low compliance and the media of the vessel (ideally to be preserved) has higher compliance. A cutter 28 having a negative angle of attack may be employed to efficiently cut through material of low compliance, while not cutting through media of high compliance, by allowing the high-compliance to stretch over the beveled surface of cutter.

Referring to FIGS. 12 through 16, one embodiment of the handle 34 will now be described in detail. The handle 34 includes a housing 40 that is sized and shaped to be held in a hand of the user. An electric motor 74 (e.g., a DC motor) is contained in the housing 40, along with a power source 76 (e.g., a battery or other source of DC power) electrically connected to the motor for powering the motor. The drive shaft 36 is operatively coupled to the motor 74 when the catheter 20 is connected to the handle 34 for driving rotation of the drive shaft and the cutter 28. In some embodiments, at maximum power the motor 74 can rotate drive shaft 36 between 1,000 rpm and 10,000 rpm or more, if desired. The manual actuator 38 (e.g., a lever, as illustrated) on the exterior of the housing 40 allows the user to control operations of the catheter 20. For example, in the illustrated embodiment the lever 38 is axially moveable relative to the housing 40. In particular, the lever 38 is movable to a neutral position (shown in FIG. 14), whereby the cutter 28 is in its non-exposed, neutral position (FIG. 3D). To expose the cutter 28 and activate the motor 74 to drive rotation of the cutter, the lever 38 is moved proximally from the neutral position to a proximal, tissue-removing position of the lever (see FIG. 15) to move the cutter proximally and out of cutting window 32 (FIG. 4B) to its tissue-removing position and simultaneously activate the motor 74. For example, proximal movement of the lever 38 to the proximal position may actuate (e.g., depress) an electrical switch 78 that electrically connects the power source 76 to the motor 74. To part off tissue, the lever 38 is moved distally from the proximal, tissue-removing position, back to its neutral position (FIG. 14) to drive (i.e., move) the cutter 28 distally into the distal portion of the catheter 20 (FIG. 3D). As the lever 38 is positioned in its neutral position, the electrical switch 78 is released (i.e., opened) so as to deactivate the electric motor 74. To pack the removed tissue in the collection chamber 53 of the distal tip member 42, the lever 38 is moved distally from the neutral position to a distal position, packing position of the lever (see FIG. 16) to drive (i.e., move) the cutter 28 distally into the collection chamber and to its packing position (FIG. 5B). It should be appreciated, while the figures illustrate the use of an lever 38 or thumb switch, other embodiments of the present invention can use other types of actuators, such as separate buttons (e.g., a close window button, debulk tissue button, and packing button), or the like.

Figure 18:
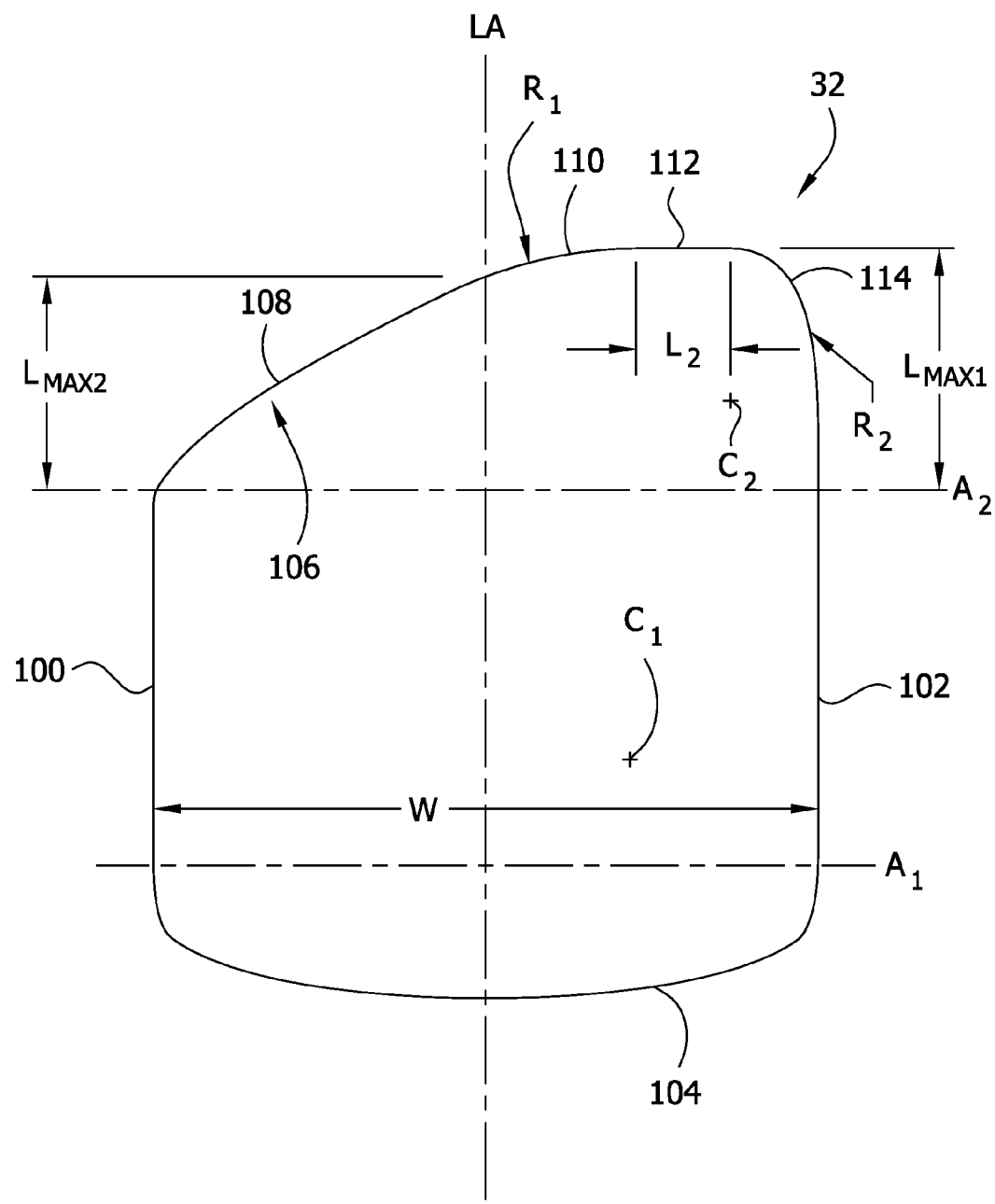
FIG. 18 is an exemplary schematic of the asymmetric window.
Figure 19:
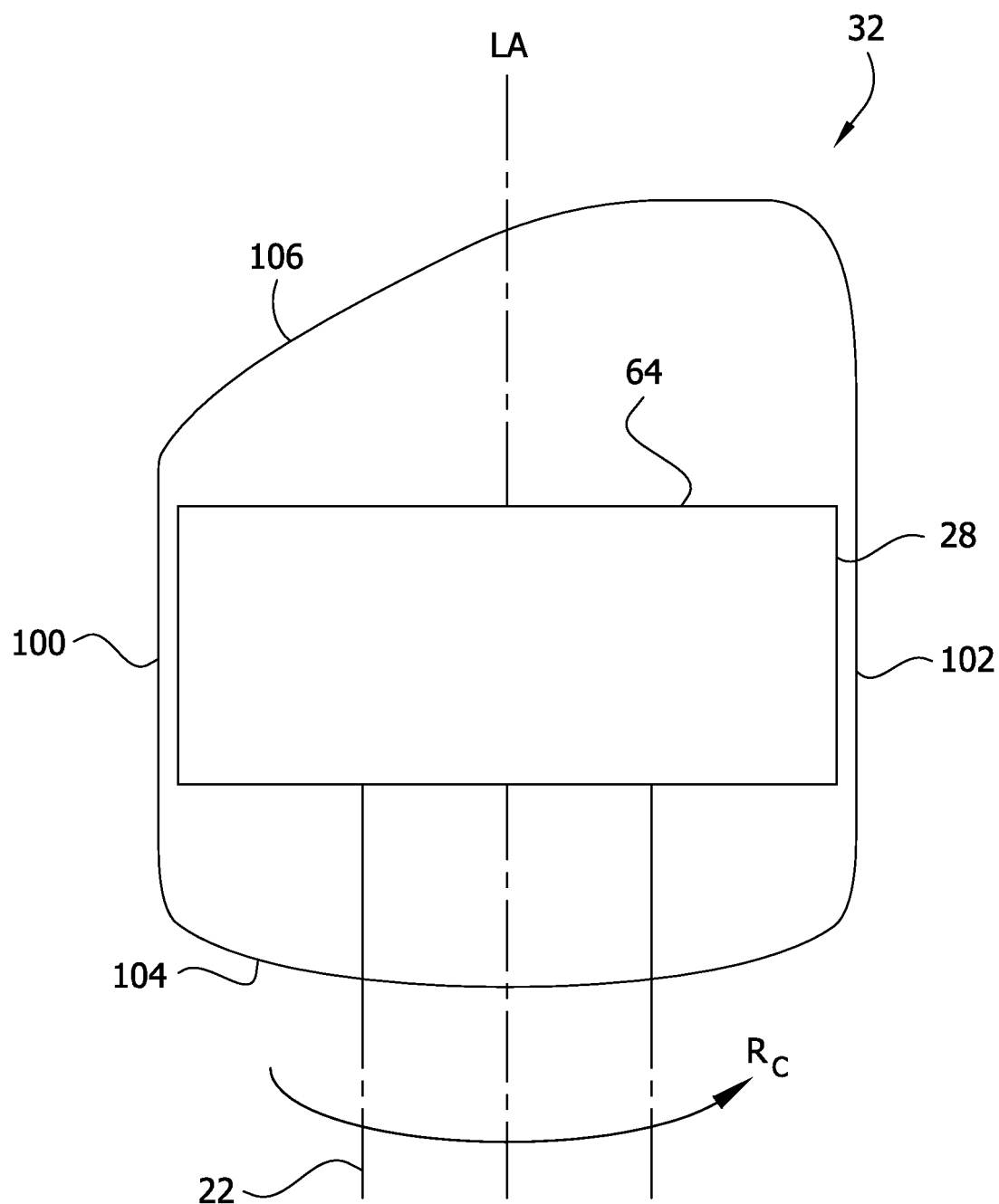
FIG. 19 is similar to FIG. 18, showing the cutter in the asymmetric window.

As set forth above, the side opening or cutting window 32 is offset or asymmetric to prevent interaction of the cutter 28 with a distal edge of the cutting window during movement of the cutter from the tissue-removing position (FIG. 4B) to the neutral position (FIG. 3B). Referring to FIGS. 17-19, the cutting window 32 is defined by a first side edge 100, a second side edge 102, a proximal edge 104 extending between the first and second side edges at a proximal end of the cutting window, and a distal edge 106 extending between the first and second side edges at a distal end of the cutting window opposite the proximal edge. A longitudinal axis LA of the cutting window 32 extends generally along the longitudinal axis of the distal portion 26 of the catheter body 22. The first and second side edges 100, 102 are generally linear and extend substantially parallel to each other and along the distal portion 26. As shown in FIG. 18, the cutting window has a width W extending between the first and second side edges 100, 102, generally orthogonal to the longitudinal axis LA of the cutting window. The width W is substantially constant or uniform longitudinally between a proximal end of the first and second side edges 100, 102 (as marked by axis $A_1$) and a distal end of the first and second side edges (as marked by axis $A_2$). In one embodiment, the width W of the cutting window 32 may be about 0.101 inches (2.5654 mm). In other embodiments, the cutting window 32 can have a different width and/or a non-constant width.

The proximal edge 104 is generally curved (e.g., concave) between the first and second side edges 100, 102 and substantially symmetric about the longitudinal axis LA, such that a proximal-most portion (e.g., point) of the proximal edge is generally aligned with the longitudinal axis and generally equidistant from the first and second side edges. Other configurations of the proximal edge are within the scope of the present invention.

The distal edge 106 is generally curved between the first and second side edges 100, 102 and substantially asymmetric about the longitudinal axis LA, such that a distal-most portion (e.g., point or length) of the distal edge is not aligned with the longitudinal axis. The distal-most portion of the distal edge 106 is offset from the longitudinal axis LA and is closer to one side edge than the other. Thus, the cutting window 32 is generally longer in a direction extending parallel to the longitudinal axis LA on one side of the longitudinal axis than it is on the other side. In one embodiment, the distal-most point of the distal edge 106 is closer to the side edge (e.g., side edge 102) toward which the cutter 28 rotates. In the illustrated embodiment, the cutter 28 rotates toward the second side edge 102, as indicated by arrow $R_C$, and the distal-most portion of the distal edge 106 is closer to the second side edge 102 than the first side edge 100. At the distal-most portion, the distal edge 106 is spaced a distance $L_{MAX1}$ from the axis $A_2$. The distance $L_{MAX1}$ is greater than a distance $L_{MAX2}$, which is the maximum distance between the distal edge 106 and the axis $A_2$ on the opposite side of the longitudinal axis LA from the distal-most portion. The distance $L_{MAX1}$ can be in a range of from about 0.005 inches (0.127 mm) to about 0.035 inches (0.889 mm).

In the non-limiting example illustrated in FIG. 18, the distal edge 106 includes a first generally linear portion 108 extending distally from the distal end of the first side edge 100, a second generally curved portion 110 extending from a distal end of the first portion, a third generally linear portion 112 extending from the second portion, and a fourth generally curved portion 114 extending from the third portion to the second side edge 102. The second portion 110 has a radius of curvature $R_1$ in a range of from about 0 inches (0 mm) (i.e., the second portion 110 is generally linear) to about 0.100 inches (2.54 mm). In one example, the radius of curvature $R_1$ of the second portion 110 is about 0.050 inches (1.27 mm). The fourth portion 114 has a radius of curvature $R_2$ in a range of from about 0.001 inches (0.0254 mm) to about 0.050 inches (1.27 mm). In one example, the radius of curvature $R_2$ of the fourth portion 114 is about 0.020 inches (0.508 mm). In the illustrated embodiment, the third portion 112 extends generally transverse to the longitudinal axis LA and defines the distal-most portion of the distal edge 106. The third portion 112 defining the distal-most portion of the distal edge 106 extends generally orthogonally relative to the longitudinal axis LA and is positioned completely on the side of the longitudinal axis LA toward which the cutter rotates (i.e., on the side toward the second side edge 102). The third portion 112 has a length $L_2$ that is the distance between a center of curvature $C_1$ of the second portion and a center of curvature $C_2$ of the fourth portion. The length $L_2$ may be about 0.013 inches (0.3302 mm). The asymmetric cutter window 32 can have other configurations and dimensions within the scope of the present invention.

The asymmetric cutter window 32 as described above prevents the cutter 28 from damaging the distal portion 26 of the catheter body 22. During movement of the cutter 28 from the tissue-removing position to the neutral position, the cutter may contact an edge of the cutter window 32 if the cutter is somehow biased or off-axis. The cutter 28 can become biased during use due to wear of the components used to deflect or position the cutter (e.g., the ramp or cam 44), due to tip deformation (e.g., because of device preparation or cleaning), or due to interaction with a patient's anatomy (e.g., tracking over the iliac arch, crossing or cutting a severely calcified lesion), for example. Because the window 32 is generally longer on the side toward which the cutter 28 rotates (i.e., the second side edge 102 in the illustrated embodiment), if the cutter is biased, the first point of contact of the cutter with an edge of the window will not be on the side toward which the cutter rotates. Upon contact with the opposite side from rotation, it is believed the cutter 28 will bounce off the side and remain functional, without ever contacting the side toward which it is spinning. In contrast, it is believed that if the cutter 28 contacts the side toward which it is spinning, it may cut into the side and get stuck and/or deform the cutter window 32, ultimately leading to a non-functional device. Therefore, the asymmetric cutter window 32 prevents damage to the catheter body 22, even if the cutter 28 is biased or off-axis.

Having described embodiments of the invention in detail, it will be apparent that modifications and variations are possible without departing from the scope of the invention defined in the appended claims. When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue from a body lumen, the tissue-removing catheter comprising:
    an elongate catheter body configured for insertion into the body lumen, the catheter body having opposite distal and proximal portions, and a longitudinal axis extending between the distal and proximal portions;
    a side opening window in the distal portion of the catheter body, wherein the side opening window is defined by opposite first and second side edges, a proximal edge extending between the first and second side edges, and a distal edge opposite the proximal edge and extending between the first and second side edges, the side opening window having a longitudinal axis extending between the distal and proximal edges; and
    a tissue-removing element at the distal portion of the catheter body for rotation generally about the longitudinal axis of the catheter body, the tissue-removing element being configured to move between a tissue-removing position, in which the tissue-removing element is exposed through the side opening window, and a neutral position, in which the tissue-removing element is positioned inside the distal portion of the catheter,
    wherein the distal edge defining the side opening window is asymmetric about the longitudinal axis of the side opening window.

2. The tissue-removing catheter set forth in claim 1, wherein a distal-most portion of the side opening window is not aligned with the longitudinal axis of the side opening window.

3. The tissue-removing catheter set forth in claim 1, wherein a maximum length of the side opening window on a first side of the longitudinal axis is greater than a maximum length of the side opening window on a second side of the longitudinal axis opposite the first side.

4. The tissue-removing catheter set forth in claim 3, wherein the tissue-removing element is configured for rotation toward the first side of the longitudinal axis.

5. The tissue-removing catheter set forth in claim 1, wherein the first and second side edges are generally linear and extending generally parallel to each other.

6. The tissue-removing catheter set forth in claim 5, wherein the tissue-removing element is configured for rotation toward the second side edge, and a distal-most point of the side opening window is positioned closer to the second side edge than to the first side edge.

7. The tissue-removing catheter set forth in claim 5, wherein the side opening window has a width extending between the first and second side edges, the width being generally constant along a length of the first and second side edges.

8. The tissue-removing catheter set forth in claim 5, wherein the distal edge of the side opening window includes a first portion extending from the first side edge and a second portion extending from the first portion, the second portion having a radius of curvature in a range of from about 0 inches (0 mm) to about 0.100 inches (2.54 mm).

9. The tissue-removing catheter set forth in claim 8, wherein the distal edge includes a third portion extending from the second portion, the third portion defining a distal-most point of the side opening window.

10. The tissue-removing catheter set forth in claim 9, wherein the distal edge includes a fourth portion extending between the third portion and the second side edge, the fourth portion having a radius of curvature in a range of from about 0.001 inches (0.0254 mm) to about 0.050 inches (1.27 mm).

11. The tissue-removing catheter set forth in claim 10, wherein a center of curvature of the second portion is spaced from a center of curvature of the fourth portion.

12. The tissue-removing catheter set forth in claim 1, wherein the tissue-removing element includes an annular cutting edge.

13. The tissue-removing catheter set forth in claim 12, wherein the annular cutting edge of the tissue-removing element faces distally.

14. The tissue-removing catheter set forth in claim 12, wherein the tissue-removing element is configured for rotation toward the second side edge, and a distal-most point of the side opening window is positioned closer to the second side edge than to the first side edge.

15. The tissue-removing catheter set forth in claim 1, wherein a distal-most portion of the side opening window is not aligned with the longitudinal axis of the side opening window,
    wherein a maximum length of the side opening window on a first side of the longitudinal axis is greater than a maximum length of the side opening window on a second side of the longitudinal axis opposite the first side.

16. The tissue-removing catheter set forth in claim 1, wherein the tissue-removing element is configured for rotation toward the second side edge, and a distal-most point of the side opening window is positioned closer to the second side edge than to the first side edge.

17. The tissue-removing catheter set forth in claim 16, wherein a maximum length of the side opening window on a first side of the longitudinal axis is greater than a maximum length of the side opening window on a second side of the longitudinal axis opposite the first side.

18. The tissue-removing catheter set forth in claim 17, wherein the tissue-removing element includes an annular cutting edge, wherein the annular cutting edge of the tissue-removing element faces distally.

19. The tissue-removing catheter set forth in claim 1, wherein a distal-most point of the side opening window is positioned closer to the second side edge than to the first side edge.

20. The tissue-removing catheter set forth in claim 1, wherein the proximal edge of the side opening window is symmetric about the longitudinal axis of the side opening window.

* * * * *